United States Patent
Capanni

(10) Patent No.: US 7,044,953 B2
(45) Date of Patent: May 16, 2006

(54) COMPRESSION BONE SCREW

(75) Inventor: Felix Capanni, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 122 days.

(21) Appl. No.: 10/375,665

(22) Filed: Feb. 27, 2003

(65) Prior Publication Data
US 2004/0172031 A1 Sep. 2, 2004

(51) Int. Cl.
A61B 17/58 (2006.01)

(52) U.S. Cl. ........................................... 606/73
(58) Field of Classification Search ................ 606/63, 606/65, 72, 73
See application file for complete search history.

(56) References Cited

U.S. PATENT DOCUMENTS

| 4,463,753 | A | * | 8/1984 | Gustilo | 606/73 |
| 4,640,271 | A | * | 2/1987 | Lower | 606/65 |
| 4,858,601 | A | * | 8/1989 | Glisson | 606/73 |
| 5,019,079 | A | * | 5/1991 | Ross | 606/72 |
| 5,417,692 | A | * | 5/1995 | Goble et al. | 606/73 |
| 5,613,968 | A | * | 3/1997 | Lin | 606/61 |
| 6,001,101 | A | * | 12/1999 | Augagneur et al. | 606/73 |
| 6,290,711 | B1 | * | 9/2001 | Caspari et al. | 606/232 |
| 6,306,140 | B1 | * | 10/2001 | Siddiqui | 606/73 |
| 6,319,254 | B1 | * | 11/2001 | Giet et al. | 606/73 |
| 6,413,260 | B1 | * | 7/2002 | Berrevoets et al. | 606/73 |
| 6,540,748 | B1 | * | 4/2003 | Lombardo | 606/61 |
| 2001/0049528 | A1 | * | 12/2001 | Kubota | 606/65 |

FOREIGN PATENT DOCUMENTS

| DE | G9290023 | 1/1994 |
| DE | 29805443 | 8/1998 |
| DE | 101 01 267 A | 7/2002 |
| DE | 10101267 | 7/2002 |
| DE | 202 13 235 U | 10/2002 |
| GB | 2 323 533 A | 9/1998 |
| WO | WO 00/67652 A | 11/2000 |

\* cited by examiner

*Primary Examiner*—Eduardo C. Robert
*Assistant Examiner*—Annette Reimers
(74) *Attorney, Agent, or Firm*—Howard & Howard

(57) ABSTRACT

A compression bone screw is described, with a shank having two opposite shank sections along its axial extent, a first thread being connected in a rotationally fixed manner to the shank in the region of the first shank section. The shank has at least one latching element for rotatably coupling a threaded component bearing a second thread to the second shank section. The invention furthermore relates to a screwdriver blade for the compression bone screw.

5 Claims, 8 Drawing Sheets

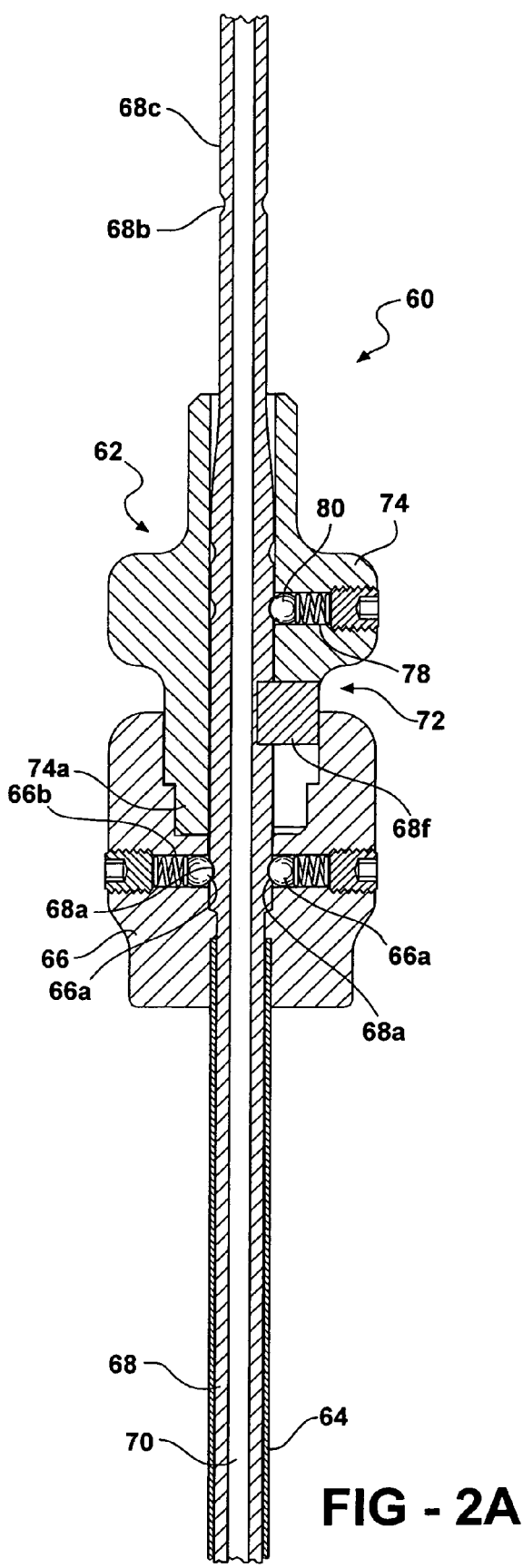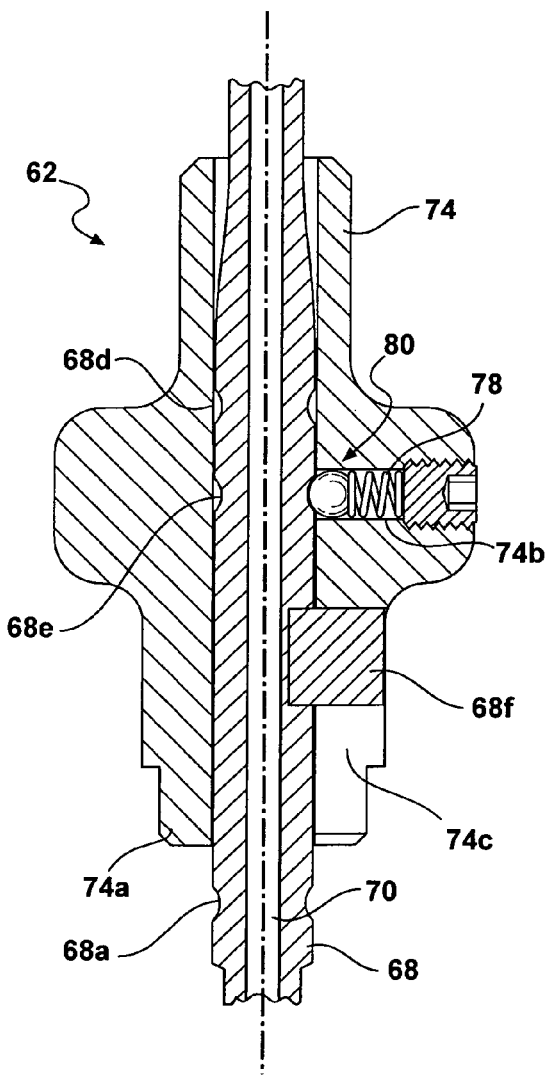
FIG - 2A
FIG - 2B

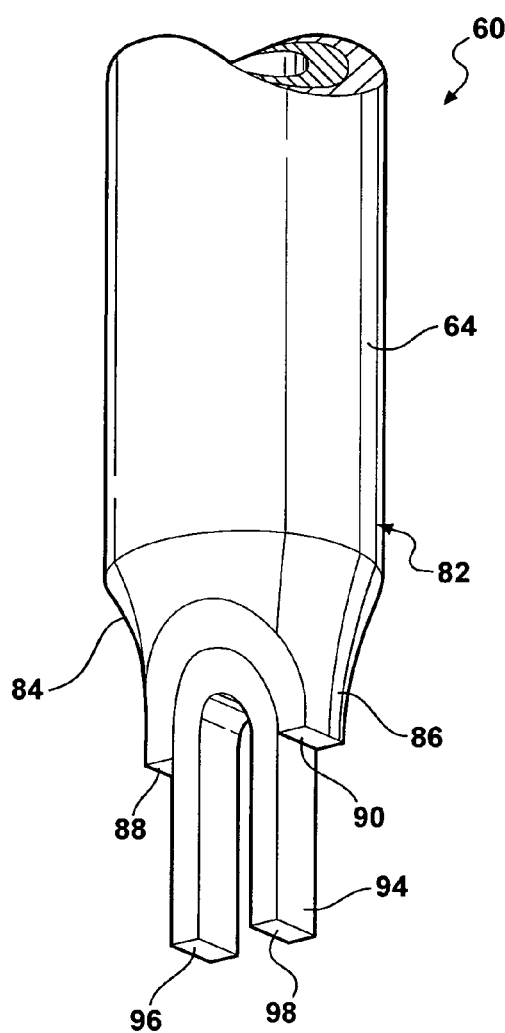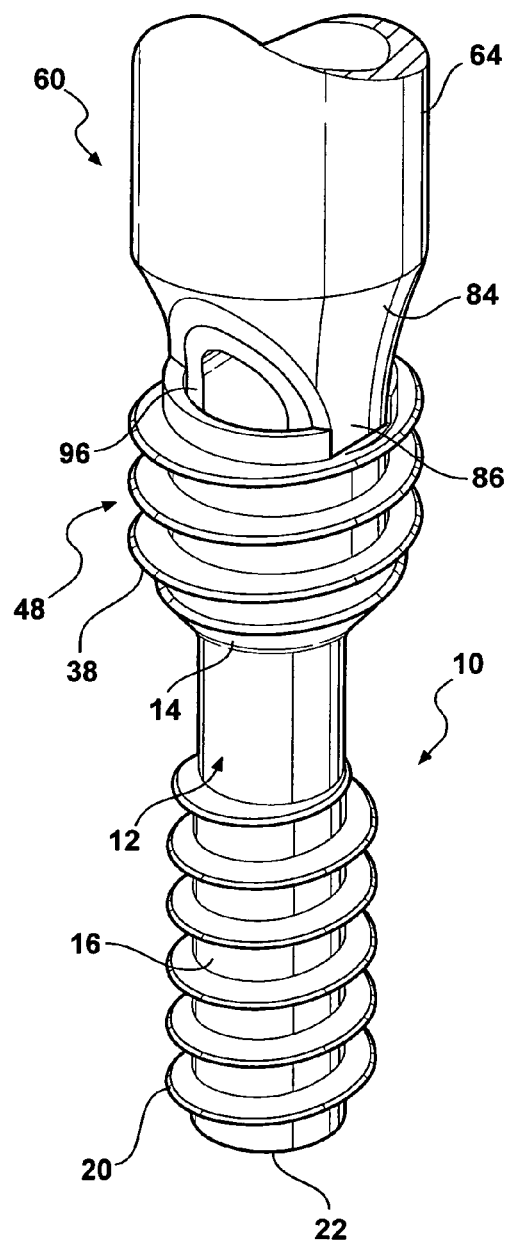
FIG - 3
FIG - 4A

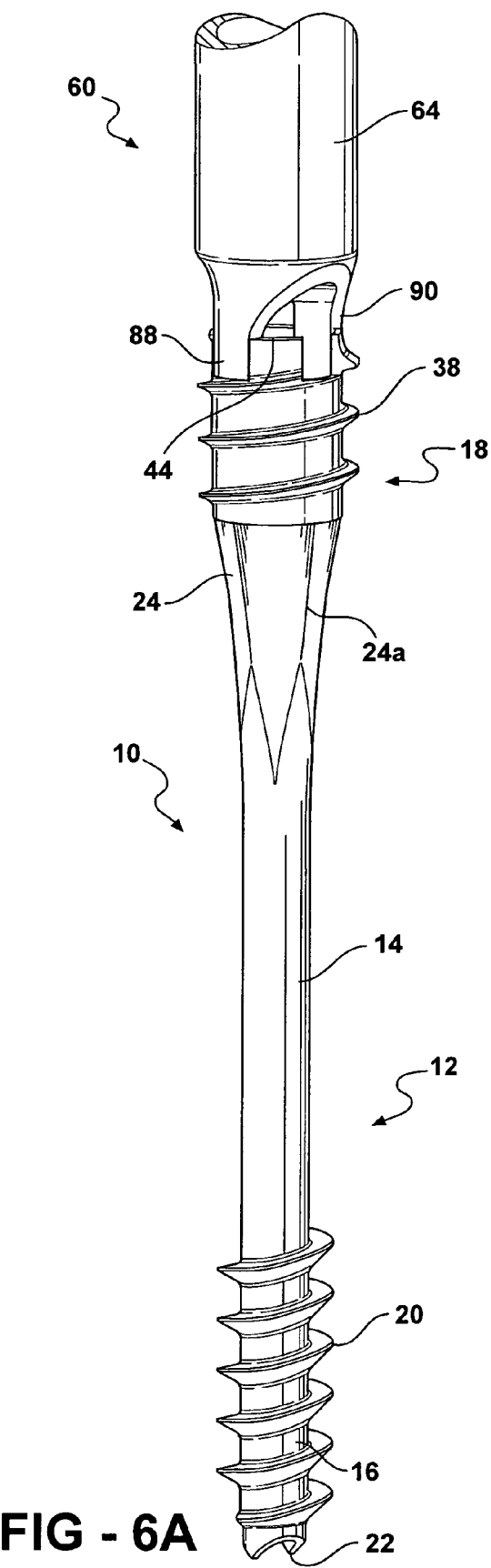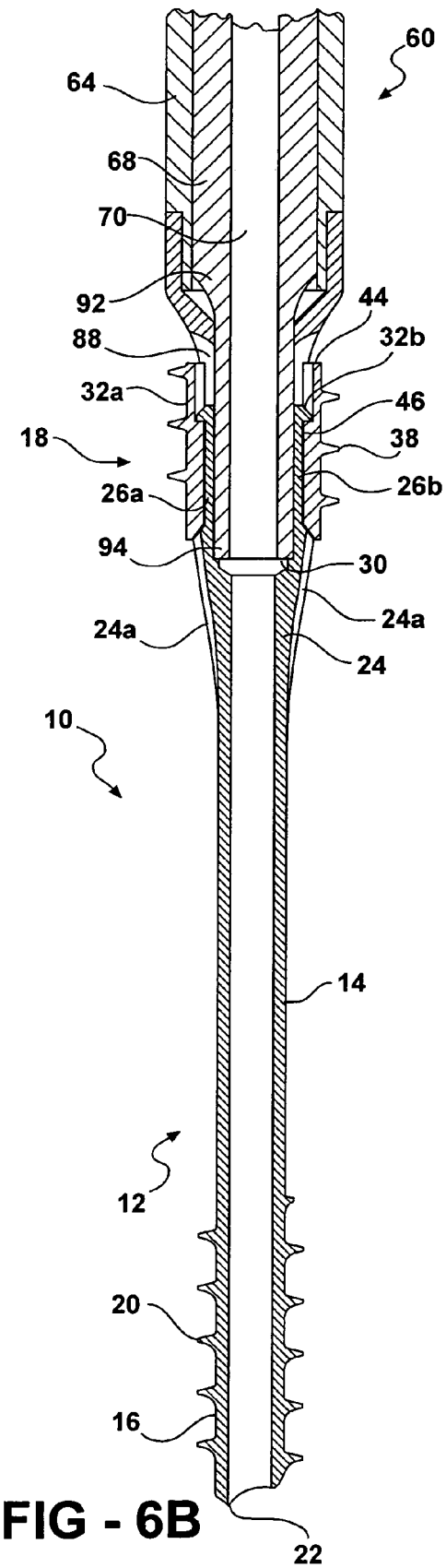
FIG - 6A
FIG - 6B

COMPRESSION BONE SCREW

FIELD OF THE INVENTION

The invention relates to a compression bone screw with a shank having two opposite shank sections along its axial extent, a first thread being connected in a rotationally fixed manner to the shank in the region of the first shank section, and the second shank section being designed for rotatable reception of a component bearing a second thread. The invention furthermore relates to a screwdriver blade for such a compression bone screw.

BACKGROUND OF THE INVENTION

Compression bone screws are used in operations in order to join together two fragments of a broken bone under compression. The compression assists the knitting of the two fragments.

Such a compression bone screw is known from U.S. Pat. No. 4,858,601. This is a double-threaded screw comprising three separate components. Two of these components each bear a thread with the same thread pitch and the same thread diameter. The two threaded components provided with a thread are each designed as a hollow-cylindrical sleeve.

The third component of the compression bone screw is a pin-shaped shank subdivided into two opposite shank halves along its axial extent and provided with a diameter enlargement at one of its two ends. The two sleeve-shaped threaded components are fitted onto the shank one after the other in such a way that the diameter enlargement of the shank acts as a stop for the two threaded components. After this, the threaded component fitted last onto the shank is connected in a rotationally fixed manner to the shank by soldering. The other of the two threaded components, in contrast, is freely rotatable about the shank as an axis of rotation.

Both the diameter enlargement of the shank and the threaded component rotatable with respect to the shank are each provided with a force-receiving structure in the form of a slot. The slots enable the separate application of a torque to the rotatable threaded component and also to the threaded component connected in a rotationally fixed manner to the shank.

To fasten the screw, two screwdrivers each with a different blade are used. The blade of the first of the two screwdrivers is designed to cooperate with the slot in the diameter enlargement of the shank, and the blade of the second of the two screwdrivers to cooperate simultaneously with the slot in the rotatable threaded component and also with the slot in the diameter enlargement of the shank. While the second screwdriver consequently permits the screwing-in of the bone screw as a whole, the first screwdriver enables a relative rotation between the two threaded components.

The object on which the invention is based is to specify a compression bone screw which is simple to produce. The further object on which the invention is based is to specify a screwdriver blade for such a compression bone screw.

SUMMARY OF THE INVENTION

It is proposed to develop a compression bone screw of the type mentioned at the outset in such a way that the shank has at least one latching element for rotatably coupling the threaded component to the second shank section.

A latching connection is therefore provided between the shank connected in a rotationally fixed manner to the first thread and the threaded component, this latching connection permitting a rotation of the threaded component about the shank as an axis of rotation. Such a compression bone screw can be assembled in a simple manner by latching the threaded component onto the shank. The latching connection between the shank and the threaded component is preferably designed in such a way that the threaded component is captively connected to the shank. The at least one latching element can be formed integrally with the shank.

The invention comprises the compression bone screw provided with a latching element according to the invention, both in the form of a screw base body composed of shank and first thread connected in a rotationally fixed manner to the shank and in the form of the fully assembled compression bone screw in which the threaded component is coupled to the shank by means of the latching connection.

Although the screw base body can, in principle, have a two-part structure composed of the shank and a separate threaded component bearing the first thread, according to a preferred embodiment of the invention the first thread is formed integrally with the shank. The fully assembled bone screw in this case comprises merely two individual parts and has a particularly simple structure.

The threaded component is preferably designed as a sleeve which either has a through opening or is closed at one of the two sleeve ends. In the case where both sleeve ends are open and the threaded component thus has a through opening, the shank can also be provided with a through opening extending in the axial direction. This enables a guide wire to be passed through the compression bone screw. Such guide wires are drilled by means of a drill directly into both bone fragments to be joined and permit a defined placement of the compression bone screw. The guide wires which are customarily used are so-called Kirschner wires with a diameter of about one millimetre.

The latching element(s) arranged on the shank can be of different design. It is thus conceivable to provide latching elements in the form of hooks, elevations or indentations.

Each latching element cooperates with a complementary latching element of the threaded component. If the latching element of the shank is designed as a hook for example, the complementary latching element of the threaded component can be an indentation in which the hook engages, or an elevation behind which the hook engages. According to a preferred embodiment of the invention, the at least one latching element of the shank extends at least in certain regions into the opening of the sleeve-shaped threaded component and establishes a latching connection with the corresponding latching element of the threaded component inside the latter.

The at least one latching element can be arranged on a shank extension extending away from the first thread in the axial direction. This extension is preferably movable in the radial direction. The extension which is movable in the radial direction can have resilient properties, so that after a deflection in the radial direction it returns to its starting position. The latching element can be arranged in the form of a radially outwardly extending latching hook at an end of the at least one extension facing away from the first thread.

Preferably, two or more extensions which are each mutually opposite with respect to a longitudinal axis of the shank are present. The provision of a plurality of extensions ensures a particularly secure connection of the threaded component to the shank. Moreover, a plurality of extensions enables a reliable guidance of the threaded component during a rotation relative to the shank.

According to a preferred embodiment, the first thread has a smaller diameter than the second thread. Furthermore, by means of suitable grinding of the screw point the compression bone screw according to the invention can be designed to be self-drilling and by means of a suitably acutely formed geometry of the thread flanks the two threads can be designed to be self-tapping. If a compression bone screw designed in this way is sunk into the bone, the first thread with the smaller diameter first cuts into the bone. Once the compression bone screw has been screwed in so far that the second thread is already gripping, the threaded hole produced in the bone by the first thread is widened by displacement and re-cut by the second thread.

The shank can be provided, between the first and the second shank section, with a diameter enlargement which acts as a stop for the threaded component in the direction of the first thread. In the case where the first thread has a smaller diameter than the second thread, the diameter enlargement can have a diameter which continuously decreases in the direction of the first thread, i.e. a conical structural shape. The diameter enlargement is preferably provided, radially on the outside, with cutting edges which have a predrilling function with respect to the second thread with the greater diameter. It is possible, for example, to provide two or three cutting edges which each extend over 180° or 120° of the outer circumference of the diameter enlargement. Preferably, five cutting edges are used.

The shank or the first thread can be provided with a first force-receiving structure which permits the application of a force and in particular a torque to the shank or the first thread. The threaded component can have a second force-receiving structure for the same purpose. By way of example, the first and second force-receiving structure can be designed slot-like, as a rib, as a polygonal socket, as a polygonal insert bit, etc. Particularly advantageous is a force-receiving structure in the form of a cross recess or in the form of a polygonal socket. The provision of separate force-receiving structures for the threaded component and also the shank or the first thread permits the separate application of a torque.

To apply a force to the force-receiving structures of the compression bone screw, provision is preferably made for a screwdriver with a screwdriver blade which comprises a first force-application structure, a second force-application structure extending through the first force-application structure and also a coupling mechanism connecting, in a first position, the first force-application structure in a rotationally fixed manner to the second force-application structure and permitting, in a second position, a relative rotation between the first force-application structure and the second force-application structure. Both the first force-application structure and the second force-application structure are each designed in such a way that a force application to one each of the force-receiving structures of the compression bone screw is possible. The screwdriver blade can have two force-application structures, each in the form, for example, of a bezel, for example a cross-bezel, or a polygonal insert bit, which each cooperate with a complementary force-receiving structure of the compression bone screw in such a way that a torque can be applied to the bone screw.

In contrast to the prior art, it is thus no longer necessary to employ two separate screwdrivers to sink the compression bone screw according to the invention. Instead, the screwdriver blade according to the invention enables both the sinking of the compression bone screw as a whole and a separate rotation of shank and threaded component, without a change of screwdriver being necessary.

According to the invention, in the first position of the coupling mechanism the compression bone screw is first sunk as a whole into the bone by means of the screwdriver. After this, in the second position of the coupling mechanism a further screwing-in of the first thread or turning back of the threaded component takes place in order to achieve a compression.

It is expedient to provide a self-locking mechanism which ensures that the compression bone screw does not unintentionally fall off the screwdriver blade. For instance, it is conceivable to use the so-called friction fit technique which is based on a frictional engagement between screwdriver blade and compression bone screw. Instead of a frictional engagement, the screwdriver blade can also be connected to the compression bone screw by means of a latching connection. By way of example, the latching connection can be designed in such a way that the screwdriver blade has at its end facing the compression bone screw an annular protrusion which cooperates with the at least one latching element of the shank of the compression bone screw. When placing the screwdriver blade onto the compression bone screw, the at least one latching element of the shank is forced radially outwards by the protrusion until the annular protrusion of the screwdriver blade is arranged in the region of an undercut of the latching element. The latching element can thereupon move back into its starting position.

Like the compression bone screw, along its axial extent the screwdriver shank and thus also the screwdriver blade can also have a through opening to enable the use of the above-described guide wire when sinking the compression bone screw.

BRIEF DESCRIPTION OF THE DRAWINGS

Advantageous developments and refinements of the invention emerge from the figures and the exemplary embodiments, in which:

FIGS. 2A and 2B show sectional illustrations of that section of a first exemplary embodiment of a screwdriver blade according to the invention which faces away from the compression bone screw;

FIG. 3 shows that section of the screwdriver blade according to FIGS. 2A and 2B which faces the compression bone screw;

FIGS. 4A and 4B show the sinking of a compression bone screw according to FIGS. 1A and 1B with the aid of the screwdriver blade according to FIGS. 2A and 2B in a side view and also in a sectional illustration;

FIGS. 6A and 6B show the sinking of the compression bone screw according to FIGS. 5A and 5B with the aid of a screwdriver blade according to the second exemplary embodiment in a side view and also in a sectional illustration;

DESCRIPTION OF PREFERRED EXEMPLARY EMBODIMENTS

Figure 1B:
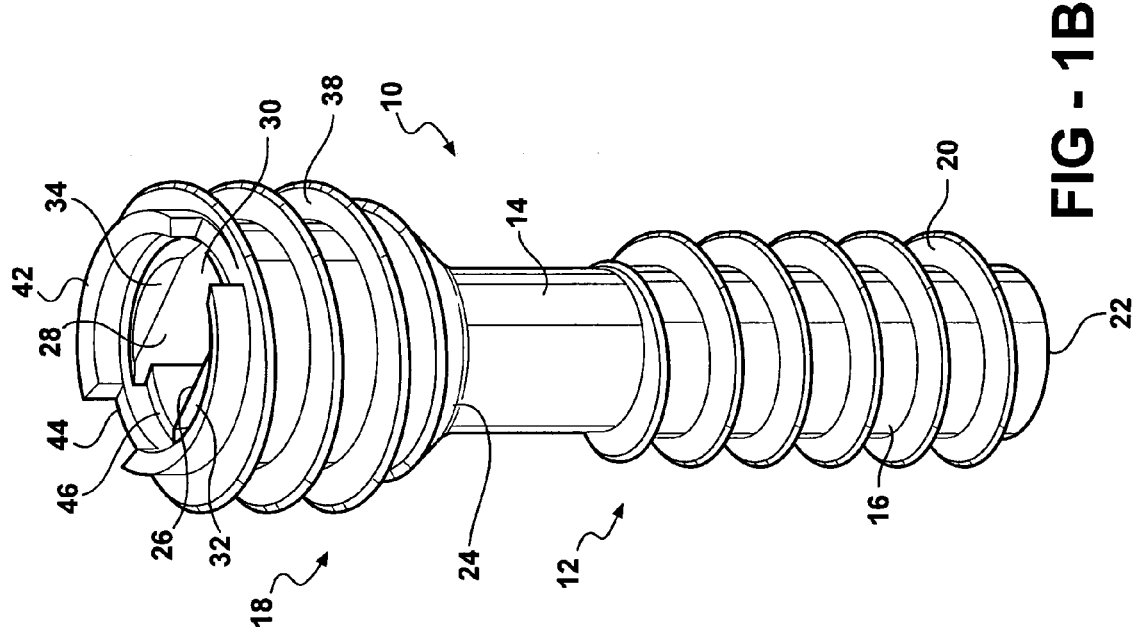
FIGS. 1A and 1B show the assembly of a first exemplary embodiment of a compression bone screw according to the invention.
Figure 1A:
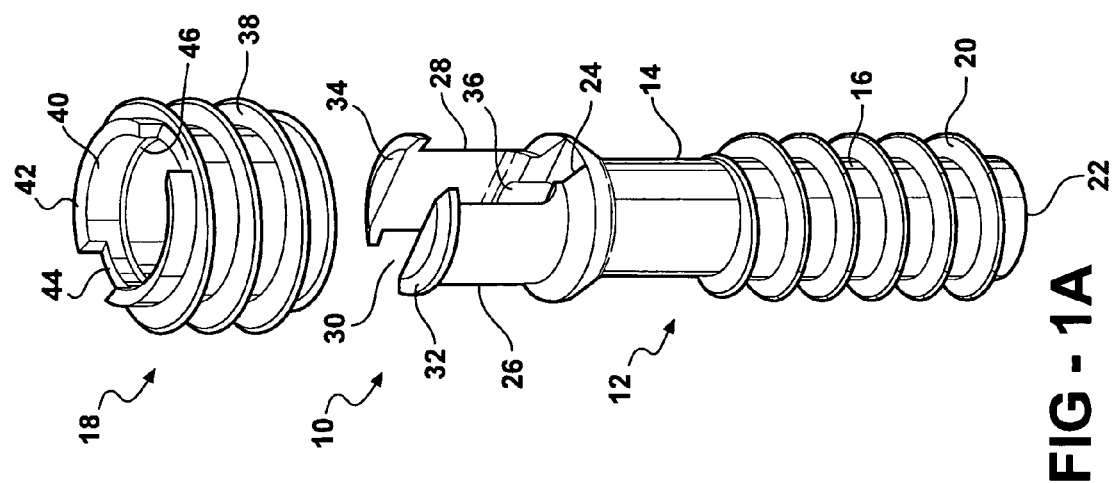

In FIGS. 1A and 1B the assembly of a first exemplary embodiment of a compression bone screw 10 according to the invention is illustrated in a side view. The two-part compression bone screw 10 comprises a shank 12 with two opposite shank sections 14, 16 and also a separate threaded component 18.

In the region of the first shank section 16, the shank 12 has an external thread 20 which is formed integrally with the shank 12. The thread 20 is of self-tapping design and leads into a screw point 22 which is ground in such a way as to be self-drilling. The second shank section 14 opposite the first shank section 16 is provided with a diameter enlargement 24 which acts as a stop for the threaded component 18. Two extensions 26, 28 extend from this diameter enlargement 24 in the axial direction away from the screw point 22 in such a way as to be offset slightly inwards radially with respect to a longitudinal axis of the shank 12. The two extensions 26, 28 are mutually opposite with respect to a longitudinal axis of the shank 12 and each have peripheries which are cylindrical radially on the outside. The two extensions 26, 28 are arranged at a distance from each other in a direction perpendicular to the longitudinal axis of the shank 12 and form a slot-shaped force-receiving structure 30. The slot-shaped force-receiving structure 30 enables the transmission of a torque to the shank 12 by means of a blade engaging in the slot-shaped force-receiving structure 30.

At their end facing away from the screw point 22, the extensions 26, 28 are each provided with a latching element in the form of a radially outwardly extending latching hook 32, 34. Each of the two extensions 26, 28 and consequently also the latching hooks 32, 34 are resiliently movable towards the longitudinal axis of the shank 12. If the extensions 26, 28 are moved radially inwards, they counter this movement with a radially outward elastic force.

As can be seen from FIG. 1A, the shank 12 has a through opening 36 running along the longitudinal axis of the shank 12 for the purpose of receiving a guide wire.

The threaded component 18 of the compression bone screw 10 illustrated in FIGS. 1A and 1B is provided with a self-tapping external thread 38. The thread 38 of the threaded component 18 is cylindrically shaped, like the thread 16 of the shank 12, i.e. the thread diameter of each of the two threads 16, 38 is constant over the length of the respective thread 16, 38. The diameter of the thread 38 of the threaded component 18 is, however, greater than the diameter of the thread 16 of the shank 12.

Like the shank 12, the threaded component 18 also has a through opening 40. The threaded component 18 is, accordingly, of sleeve-shaped design and permits the passage of a guide wire through the threaded component 18. The sleeve wall 42 of the threaded component 18 has, at its end facing away from the thread point 22, a slot-shaped force-receiving structure 44 extending perpendicularly to the longitudinal axis of the threaded component 18. The width of the slot-shaped force-receiving structure 44 of the threaded component 18 corresponds approximately to the width of the slot-shaped force-receiving structure 30 of the shank 12.

The sleeve-shaped threaded component 18 is provided, at its end facing away from the screw point 22, with an internal diameter enlargement forming a shoulder 46. As described below, this shoulder 46 acts as a latching element of the threaded component 18 which is complementary to the latching hooks 32, 34 of the shank 12. To establish a latching connection between the threaded component 18 and the shank 12, the threaded component 18 is latched onto the shank 12 in the axial direction. When fitting-the-threaded component 18 onto the shank 12, the two extensions 26, 28 with the latching hooks 32, 34 of the shank 12 are first pushed radially inwards by the inner wall of the threaded component 18. If the threaded component 18 is now pushed further in the direction of the screw point 22, the extensions 26, 28 with the latching hooks 32, 34 of the shank 12 move radially outwards again and engage behind the shoulder 46 of the threaded component 18. The latching connection between the threaded component 18 and the shank 12 is thus established. The threaded component 18 is consequently rotatably arranged between the latching hooks 32, 34 and the diameter enlargement 24 of the shank 12 with little axial play.

In order that the extensions 26, 28 of the shank 12 oppose a rotation of the threaded component 18 with as little frictional resistance as possible, the internal diameter of the sleeve-shaped threaded component is slightly greater than the distance of the two cylindrical peripheries situated radially on the outside of the two extensions 26, 28 from each other.

In FIG. 1B the fully assembled compression bone screw 10 in the as-delivered condition is illustrated. Clearly visible are the force-receiving structures 44, 30 of threaded component 18 and shank 12. To apply a torque to these force-receiving structures 30, 44, the screwdriver blade illustrated in FIGS. 2 to 4 can be used.

In FIGS. 2A and 2B an upper section 62 of the screwdriver blade 60 facing away from the compression bone screw is depicted.

According to FIG. 2A, the screwdriver blade 60 comprises a cylindrical outer sleeve 64 having, at its end facing away from the compression bone screw, a diameter enlargement 66 connected to the sleeve 64 in a rotationally fixed manner. Arranged within the sleeve 64 is a shank 68. The shank 68 has along its longitudinal axis a through opening 70 which permits the passage of a guide wire through the screwdriver 60.

Above the sleeve 64, the shank is provided with an annularly encircling groove 68a. Balls 66a, which are arranged in radially extending openings of the diameter enlargement 66, are guided in the groove 68a. These balls 66a are prestressed radially inwards by a spring 66b in each case, so that they are always in contact with the groove 68a. The-balls 66a serve, together with the groove 68a, for low-friction support of the diameter enlargement 66 in the case of a relative rotation with respect to the shank 68.

A coupling mechanism 72 permits, in a first position, a rotationally fixed connection of the sleeve 64 to the shank 68 and, in a second position, a relative rotation between sleeve 64 and shank 68. The coupling mechanism 72 comprises a sleeve-shaped slide switch 74 which surrounds the shank 68 radially on the outside at its end facing away from the bone screw and is connected to the shank 68 in a rotationally fixed manner.

The slide switch 74 is movable in the axial direction between an upper and lower position with respect to the bone screw. The two positions are designed as latching positions. In the lower position illustrated in FIG. 2A, one end 74a of the slide switch 74 facing the bone screw is in positive engagement with a corresponding recess of the diameter enlargement 66. Consequently, diameter enlargement 66 and slide switch 74, or sleeve 64 and shank 68, are coupled to one another in a rotationally fixed manner. If the slide switch 74 is now displaced along the shank 68 in the axial direction upwards into its upper latching position, the end 74*a* of the slide switch 74 facing the bone screw comes out of engagement with the corresponding recess of the diameter enlargement 66. Consequently, diameter enlargement 66 and slide switch 74, or sleeve 64 and shank 68, are rotatable independent of each other.

The screwdriver blade 60 illustrated in FIG. 2A forms the main part of a screwdriver according to the invention. To mount the screwdriver, the screwdriver blade 60 is provided with a handpiece, not illustrated in FIG. 2A, which is latched onto the end of the shank 68 facing away from the bone compression screw. To enable latching of the slide switch 74 onto the shank 68, the latter has at its end facing away from the compression bone screw a further groove 68*b*, in which balls of the handpiece engage in a latching manner, analogously to the balls 66*a* of the diameter enlargement 66. For the rotationally fixed connection of the handpiece to the shank 68, the shank 68 has at its end opposite the bone compression screw a surface structure in the form of a polygonal insert bit 68*c*, which cooperates with a corresponding structure in the form of a polygonal socket of the handpiece.

In FIG. 2B the structure of the slide switch 74 of the screwdriver blade 60 of FIG. 2A is sketched in more detail. To realize the latching mechanism of the slide switch, a ball 80 and a spring 78 prestressing the ball 80 radially inwards are arranged in an opening 74*b* of the slide switch 74 extending in the radial direction. The shank 68 has, radially on the outside, two annularly encircling grooves 68*d* and 68*e* spaced in the axial direction. In the lower latching position illustrated in FIG. 2B, the ball 80 is prestressed by the spring 78 into the lower groove 68*e*. If the slide switch 74 is displaced upwards in the axial direction, the ball 80 can latch into the upper groove 68*d*. This position of the slide switch 74 corresponds to the upper latching position.

A rib 68*f* extending in the axial direction and connected rigidly to the shank 68 is received in an axial slot 74*c* of the slide switch 74. This coupling of shank 68 and slide switch 74 permits an axial displacement of the slide switch 74 relative to the shank 68 and at the same time ensures a rotationally fixed connection between slide switch 74 and shank 68. Furthermore, the axial movability of the slide switch 74 can be limited via the length of the axial slot 74*c*.

In FIG. 3 a section 82 of the screwdriver blade 60 according to the invention which faces the compression bone screw is illustrated. At its end facing the compression bone screw, the sleeve 64 has a conically tapering region 84 which leads into a force-application structure 86 running perpendicularly to the longitudinal axis of the screwdriver blade 60. The sleeve-like, bezel-shaped force-application structure 86 has a substantially U-shaped form with two mutually opposite legs 88, 90 extending in the direction of the compression bone screw. Via the bezel-shaped force-application structure 86, the sleeve 64 cooperates with the slot-shaped force-receiving structure 44 of the threaded component 18, illustrated in FIGS. 1A and 1B.

Figure 4B:
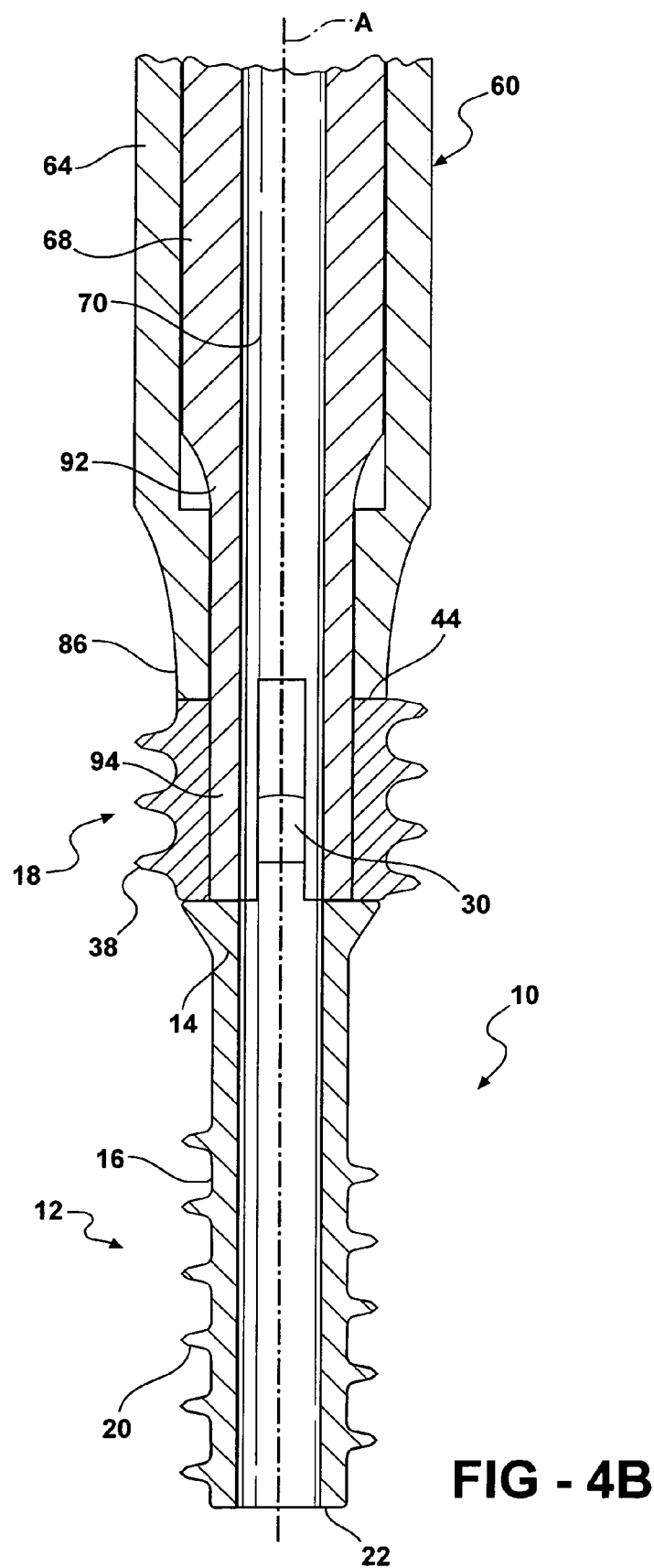

The shank 68, extending through the sleeve 64, of the screwdriver blade 60 also has a section 92 tapering conically in the direction of the compression bone screw (FIG. 4B). This conically tapering section 92 leads into a substantially U-shaped force-application structure 94 with two legs 96, 98 mutually opposite with respect to the longitudinal axis A of the screwdriver blade 60. Via this likewise bezel-shaped force-application structure 94, the screwdriver shank 68 cooperates with the force-receiving structure 30 of the screw shank 12, illustrated in FIGS. 1A and 1B.

In FIGS. 4A and 4B the engaging of the two force-application structures 86, 94 of the screwdriver 60 with the corresponding force-receiving structures 30, 44 of the compression bone screw 10 is sketched. Firstly, as illustrated in FIG. 1B, the two slot-shaped force-receiving structures 30, 44 of the compression bone screw 12 are oriented relative to each other in such a way that they are aligned perpendicularly to the longitudinal axis of the compression bone screw. The two bezel-shaped force-application structures 86, 94 of the screwdriver blade 60 are, as illustrated in FIG. 3, also oriented relative to each other in such a way that they are aligned perpendicularly to the longitudinal axis of the screwdriver blade 60. After this, the screwdriver blade 60 is placed onto that end of the compression bone screw 12 which faces away from the screw point 22, so that the force-application structure 86 engages in the force-receiving structure 44 and the force-application structure 94 engages in the force-receiving structure 30.

The coupling mechanism 72 illustrated in FIGS. 2A and 2B is initially in its first, lower latching position. The two force-application structures 86, 94 of the screwdriver blade 60 are consequently connected to each other in a rotationally fixed manner. By rotating the screwdriver blade 60 about its longitudinal axis A, the compression bone screw 10 can be screwed-as a whole into the two bone fragments to be joined, since a rotational movement of the screwdriver blade 60 is transmitted both to the thread 20 formed integrally with the shank 12 of the compression bone screw 10 and to the thread 38 formed integrally with the threaded component 18 of the compression bone screw 10.

Once the bone screw 10 has been sunk into the bone fragments, the coupling mechanism 72 of the screwdriver blade 60 is moved into the second, upper latching position, so that the two force-application structures 86, 94 of the screwdriver blade 60 are rotatable independently of each other. The radially inner force-application structure 94 with respect to the longitudinal axis A of the screwdriver blade can be rotated by means of the slide switch 74 or by means of the illustrated handpiece. A rotation of the radially outer force-application structure 86 of the sleeve 64 is effected by means of the diameter enlargement 66 of the sleeve 64.

To obtain a compressive force, after the sinking of the compression bone screw 10 as a whole, either the thread 20 formed on the shank 12 is sunk separately further into the corresponding bone fragment or the threaded component 18 provided with the thread 38 is screwed out of the corresponding bone fragment. The screwdriver blade 60 according to the invention therefore enables both the sinking of the compression bone screw 10 as a whole and the production of a compressive force without a change of screwdriver having to take place.

In contrast to the exemplary embodiments illustrated in FIGS. 1 to 4, other designs of the latching connection between screw shank 12 and threaded component 18 are also conceivable. In particular, it would be possible for example to increase the number of extensions 26, 28 bearing the latching elements 32, 34. A different form of the force-receiving structures 30, 44 and also-of the force-application structures 86, 94 is also conceivable. Thus, in FIGS. 5A, 5B, 6A and 6B a second exemplary embodiment of a compression bone screw 10 according to the invention with a first force-receiving structure 30 formed in the shank 12 as a hexagon socket and a second force-receiving structure 44 formed in the threaded component 18 as a cross recess is illustrated.

The compression bone screw 10 according to the second exemplary embodiment corresponds essentially to the compression bone screw according to the first exemplary embodiment (FIGS. 1A and 1B). Corresponding elements have thus been provided with the same reference symbols. The compression bone screw 10 according to the second exemplary embodiment has a greater overall length however. Furthermore, the diameter enlargement 24 of the compression bone screw according to the second exemplary embodiment has an elongated conical structural shape. Radially on the outside, the conical diameter enlargement 24 is provided with a total of five cutting edges 24*a* which have a predrilling function with respect to the thread 38 of the threaded component 18.

Figure 5A:
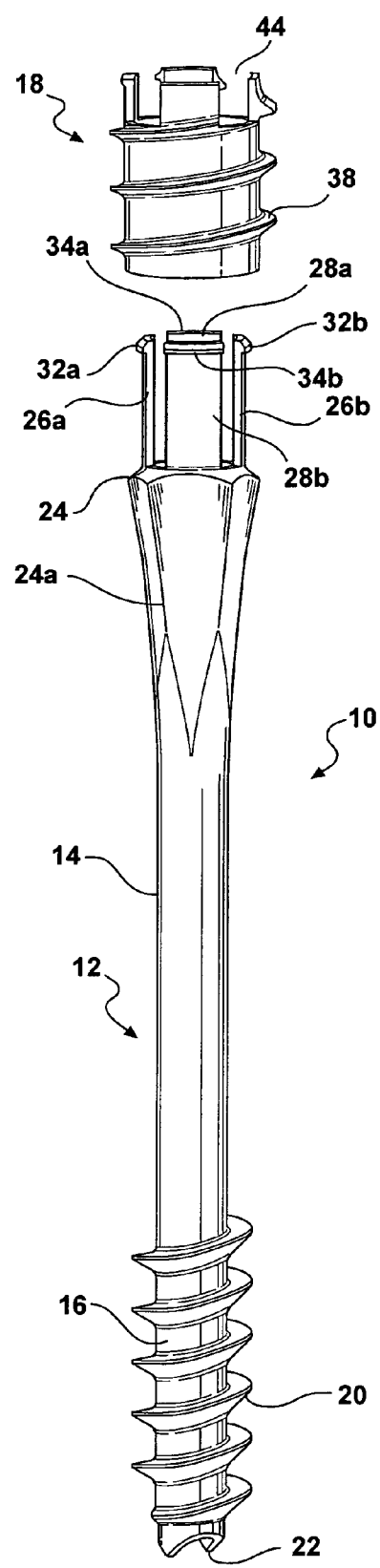
FIGS. 5A and 5B show the assembly of a second exemplary embodiment of a compression bone screw according to the invention.
Figure 5B:
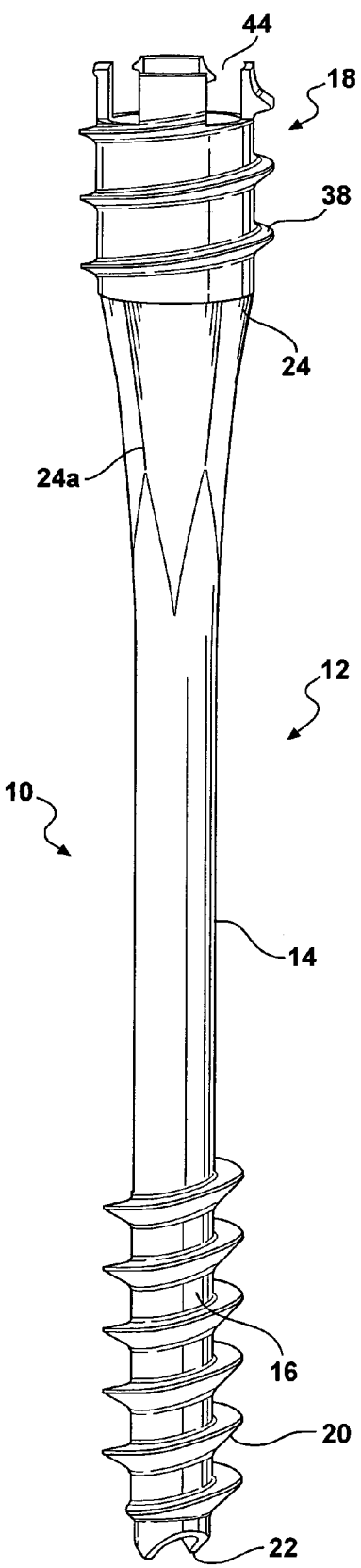
Figure 7B:
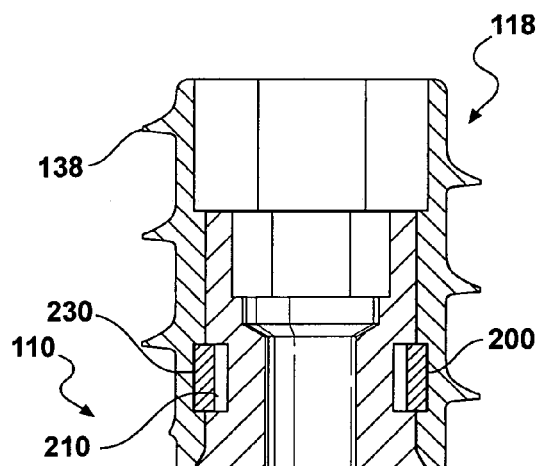
FIGS. 7A to 7C show various illustrations of different components of a third exemplary embodiment of a compression bone screw according to the invention.
Figure 7B:
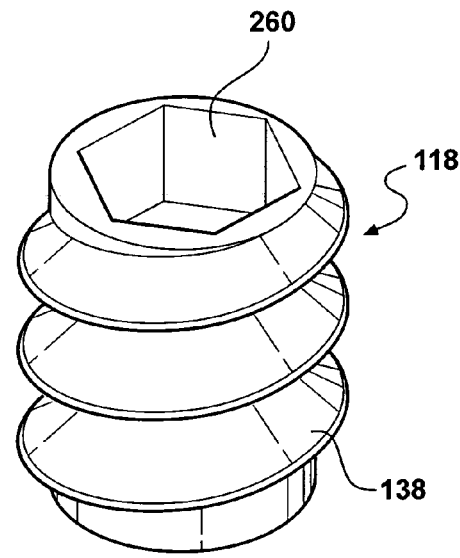
Figure 7A:
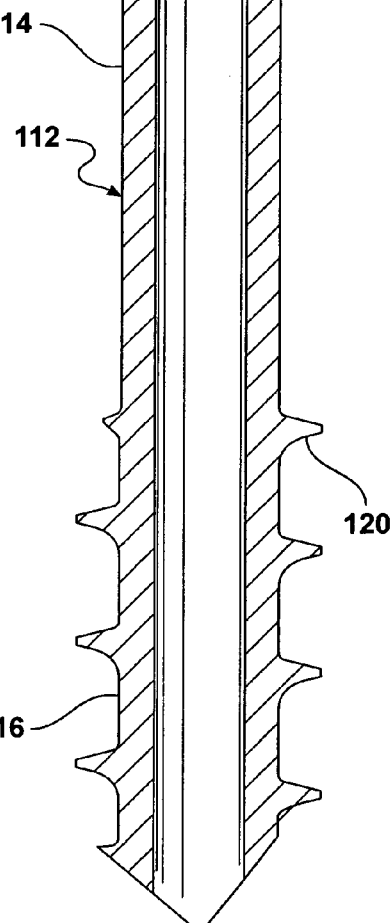
Figure 7C:
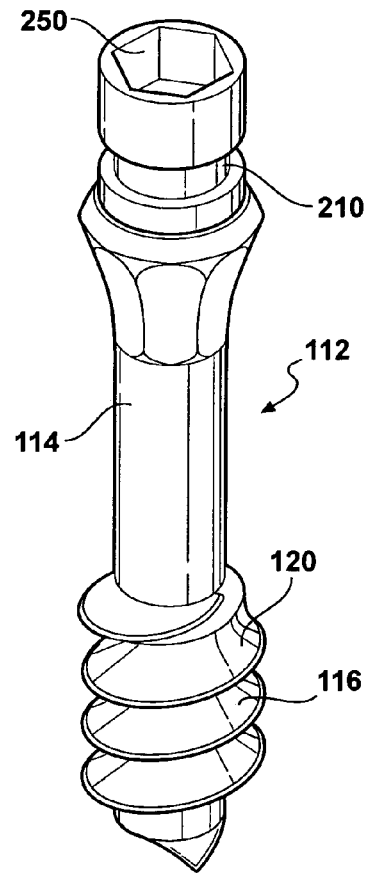

As can be seen from FIG. 5A, the shank 12 has two extension pairs 26*a*, 26*b*, 28*a*, 28*b* which extend away from the screw point 22, starting from that end of the shank 12 which faces away from the screw point 22. At their ends facing away from the screw point 22, the extensions 26*a*, 26*b*, 28*a*, 28*b* are provided with a latching hook 32*a*, 32*b*, 34*a*, 34*b* in order to enable a latching connection of the threaded component 18 to the shank 12. The force-receiving structure 30 of the shank 12 is no longer formed by the extensions 26*a*, 26*b*, 28*a*, 28*b* in the case of the compression bone screw 10 according to the second exemplary embodiment, but by a hexagon socket structure 30 arranged at the bottom of a diameter enlargement of the cannulated shank 12 (FIG. 6B). As can be seen from FIGS. 5A and 5B, the threaded component 18 has a force-receiving structure in the form of a cross recess 44.

Owing to the fact that the design of the force-receiving structures 30, 44 of the compression bone screw 10 according to the second exemplary embodiment differs from that of the first exemplary embodiment, the second exemplary embodiment of a screwdriver blade 60 illustrated in FIGS. 6A and 6B also has modified force-application structures as compared with the first exemplary embodiment. As FIG. 6A shows, the sleeve 64 of the screwdriver blade 60 now has a total of four legs (two of these legs 88, 90 are illustrated in FIG. 6A). As FIG. 6B shows, the shank 68 of the screwdriver blade 60 extending through the sleeve 64 has a force-application structure in the form of a hexagon insert bit 94 at its end facing the compression bone screw 10. When placing the screwdriver blade 60 onto the compression bone screw 10, this hexagon insert bit 94 comes into engagement with the corresponding hexagon socket 30 of the shank 12 and the four legs 88, 90 come into engagement with the cross-recess structure 44 of the threaded component 18 of the compression bone screw 10.

The functioning of the system composed of compression bone screw 10 and screwdriver blade 60 illustrated in FIGS. 6A and 6B corresponds to the functioning described with reference to FIGS. 4A and 4B.

A third exemplary embodiment of a compression bone screw 110 according to the invention is described below with reference to FIGS. 7A to 7C and 8A to 8D. The compression bone screw 110 according to the third exemplary embodiment corresponds in several aspects to the compression bone screws according to the first two exemplary embodiments. Corresponding elements have thus been provided with similar reference symbols.

The essential difference lies in the mechanism for connecting the shank 112 to the separate threaded component 118. While the connection of shank and threaded component has been accomplished by means of snap hooks in the case of the bone screws of the first two exemplary embodiments, a coupling component deformable in the radial direction and in the form, for example, of a ring 200 is now employed as an additional element. It has been found that substantially higher compressive forces can be transmitted by means of the ring 200.

A further difference of the bone screw 110 according to the third exemplary embodiment relates to the screw-foot thread 120. It has been found that, in the case of a double-threaded screw in which the thread of the threaded component has a greater diameter than the thread of the shank, problems arise in certain situations when unscrewing the screw. In the case of the compression bone screw 110 according to the third exemplary embodiment, the diameter of the upper turns of the thread 120 of the shank 112 is therefore increased. This increase in diameter increases the screwing-in torque only very slightly, but on the other hand facilitates the removal of the bone screw 110 from the bone quite considerably.

The assembly of a compression bone screw 110 according to the third exemplary embodiment is explained below with reference to FIGS. 7B, 7C and 8A to 8D. As already mentioned, the cannulated compression bone screw 110 according to the third exemplary embodiment comprises three components, namely a screw foot in the form of the shank 112 with the thread 120, a screw head in the form of a separate threaded component 118 with a thread 138, and also an expandable (not closed) securing ring 200. Both threads 120, 138 have the same pitch and the same hand.

Figure 8A:
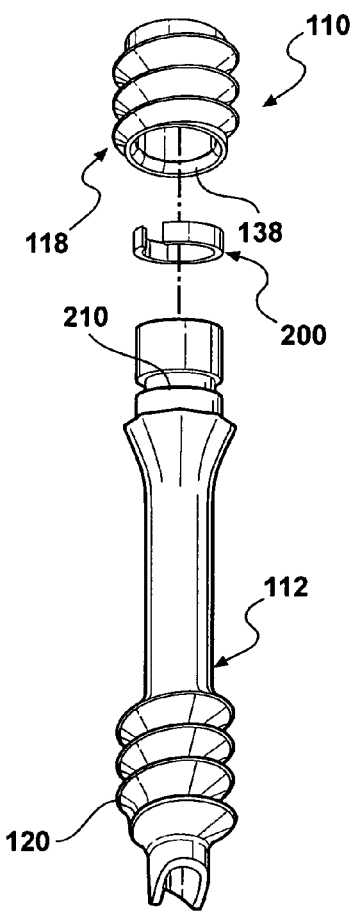
FIGS. 8A to 8D show the assembly of the compression bone screw illustrated in FIGS. 7A to 7C.
Figure 8B:
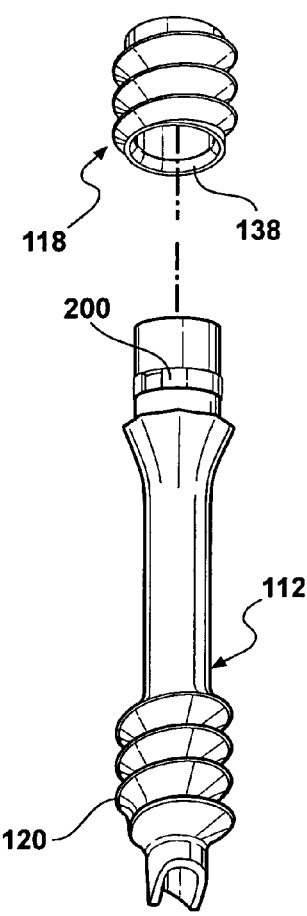
Figure 8C:
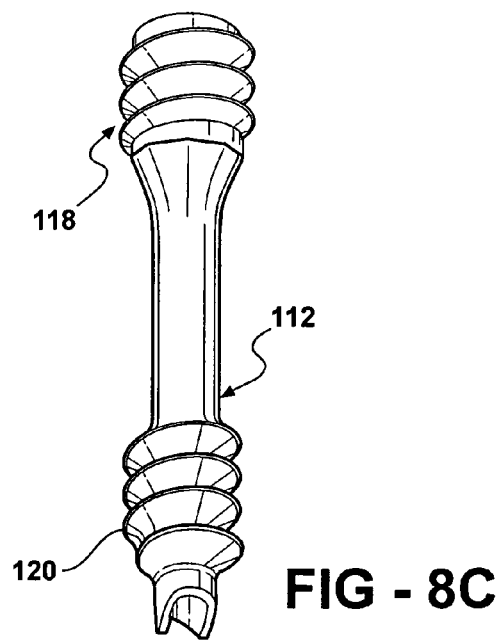
Figure 8D:
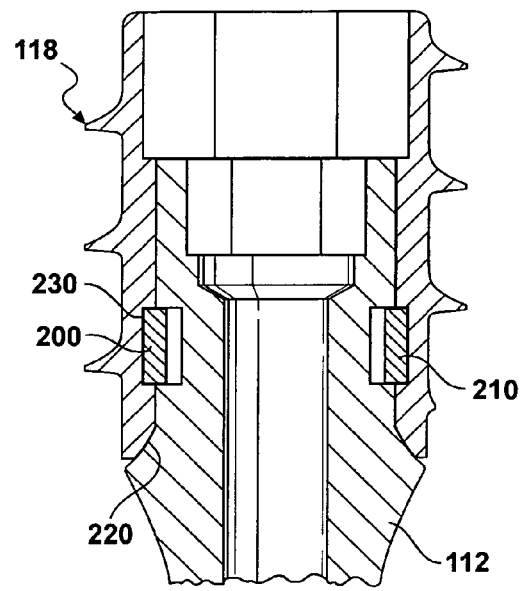

In a first step (FIG. 8B), the securing ring 200, which is radially expandable in the manner of a snap ring, is pushed into a groove 210 provided for it, which is formed on the shank 112 and runs in the circumferential direction of the shank 112. To do this, a slight elastic widening of the securing ring 200 is initially required when it is being pushed onto the shank 112. As soon as the securing ring 200 is in the region of the groove 210, the elastic properties of the securing ring 200 cause it to contract again and as it does so to latch into the groove 210 and be captively received in the groove 210. As can be seen in FIG. 8B, the internal diameter of the securing ring 200 is slightly greater than the external diameter of the base of the groove 210. The securing ring 200 is therefore deformable in the direction of the base of the groove 210.

Furthermore, the external diameter of the securing ring 200 is somewhat greater than the external diameter of that region of the shank 112 which surrounds the groove 210. In other words, the coupling element in the form of the ring 200 protrudes in the radial direction somewhat beyond the shank 112 and can additionally be elastically deformed in the radial direction inwards, i.e. in the direction of the base of the groove 210.

The threaded component 118 is fitted onto the shank 112. When fitting on the threaded component 118, conical flanks 220 of the threaded component 118 cooperate with the securing ring 200 in such a way that the latter is deformed radially inwards, i.e. assumes a smaller diameter. The threaded component 118 has, radially in the inside, a groove 230 which runs in the circumferential direction of the threaded component 118 and into which the securing ring 200 can expand in a latching manner as soon as the axial position of the securing ring 200 coincides with the axial position of the groove 230 of the threaded component 118 when fitting on the threaded component 118. After the radial expansion of the securing ring 200, the threaded component 118 is captively coupled to the shank 112 by means of the securing ring 200 engaging simultaneously in the groove 210 and the groove 230. Any compressive forces between the threaded component 118 and the shank 112 are transmitted by means of the securing ring 200. Both the shank 112 and the threaded component 118 are each provided with a force-application structure in the form of a hexagon socket 250, 260.

The invention claimed is:

1. A compression bone screw, comprising;
a shank having opposite first and second shank sections along its axial extent with a first thread being connected in a rotationally fixed manner to the shank in the region of the first shank section,
a threaded component bearing a second thread and the second shank section being designed for rotatable reception of the threaded component, and
a snap ring separate from the shank and threaded component and radially expandable for fitting onto the shank to couple the threaded component to the shank.

2. A compression bone screw according to claim 1 wherein the shank defines a radially outward indentation for latching reception of the snap ring and the threaded component defines a radially inward indentation for latching reception of the snap ring.

3. A compression bone screw according to claim 1 wherein the snap ring is disposed radially between the shank and the threaded component and prevents relative axial movement between the shank and the threaded component.

4. A compression bone screw, comprising;
a shank having opposite first and second shank sections along its axial extent with a first thread being connected in a rotationally fixed manner to the shank in the region of the first shank section,
a threaded component bearing a second dread and the second shank section being designed for rotatable reception of the threaded component, and
a snap ring radially expandable for fitting onto the shank to couple the threaded component to the shank and prevent relative axial movement between the threaded component and the shank.

5. A compression bone screw according to claim 4 wherein the shank defines a radially outward indentation for latching reception of the snap ring and the threaded component defines a radially inward indentation for latching reception of the snap ring.

* * * * *

UNITED STATES PATENT AND TRADEMARK OFFICE
CERTIFICATE OF CORRECTION

| | |
|---|---|
| PATENT NO. | : 7,044,953 B2 |
| APPLICATION NO. | : 10/375665 |
| DATED | : May 16, 2006 |
| INVENTOR(S) | : Felix Capanni |

Page 1 of 1

It is certified that error appears in the above-identified patent and that said Letters Patent is hereby corrected as shown below:

Column 12, line 7, Claim 4, delete "dread" and please replace with - -thread- -.

Signed and Sealed this

Fifteenth Day of August, 2006

JON W. DUDAS
*Director of the United States Patent and Trademark Office*